US006773724B2

(12) United States Patent
Franckowiak et al.

(10) Patent No.: US 6,773,724 B2
(45) Date of Patent: Aug. 10, 2004

(54) STABLE SALTS OF O-ACETYLSALICYLIC ACID WITH BASIC AMINO ACIDS

(75) Inventors: Gerhard Franckowiak, Wuppertal (DE); Hubert Appolt, Kürten (DE); Gregor Leifker, Milan (IT); Hans-Peter Wirges, Krefeld (DE); Wolfram Ledwoch, Langenfeld (DE)

(73) Assignee: Bayer AG, Leverkusen (DE)

( * ) Notice: Subject to any disclaimer, the term of this patent is extended or adjusted under 35 U.S.C. 154(b) by 0 days.

(21) Appl. No.: 09/906,497

(22) Filed: Jul. 16, 2001

(65) Prior Publication Data

US 2002/0091108 A1 Jul. 11, 2002

(30) Foreign Application Priority Data

Jul. 18, 2000  (DE) .......................................... 100 34 802

(51) Int. Cl.[7] ................................................ A61K 9/14
(52) U.S. Cl. ...................... 424/489; 424/499; 424/98; 424/400
(58) Field of Search ................ 424/489, 422, 424/400, 499

(56) References Cited

U.S. PATENT DOCUMENTS

| 4,265,888 A | | 5/1981 | Kagitani et al. ............ 424/233 |
| 5,716,636 A | * | 2/1998 | Horstmann et al. ......... 424/448 |
| 5,750,559 A | * | 5/1998 | Bianco ....................... 514/428 |

FOREIGN PATENT DOCUMENTS

| JP | HP 48056815 | | 11/1971 |
| JP | 356113741 A | * | 9/1981 |

OTHER PUBLICATIONS

Moll, F. et al., "Wechselwirkungen zwichen Acetylsalicylsaure und Lysin in Losung," Arch. Pharm. 318, 120–27 (1985).

* cited by examiner

Primary Examiner—James M. Spear
Assistant Examiner—Liliana Di Nola-Baron

(57) ABSTRACT

The present invention relates to stable salts of O-acetylsalicylic acid with basic amino acids, a process for their preparation and their use as medicaments.

21 Claims, 7 Drawing Sheets

STABLE SALTS OF O-ACETYLSALICYLIC ACID WITH BASIC AMINO ACIDS

The present invention relates to stable salts of O-acetylsalicylic acid with basic amino acids, a process for their preparation, and their use as medicaments.

The analgesic action of O-acetylsalicylic acid (Aspirin®) has been utilized therapeutically for a long time. Thus O-acetylsalicylic acid is used as an analgesic, antipyretic, antirheumatic, and also as a non-steroidal anti-inflammatory agent, for example for the treatment of arthritis, neuralgia and myalgia.

However, O-acetylsalicylic acid is only soluble to a limited extent and thus is only suitable for oral administration. However, it has been disclosed (cf. JP-A-48056815) that salts of O-acetylsalicylic acid with basic amino acids are suitable for parenteral administration. As basic amino acids, in particular L-lysine, D,L-lysine and arginine are employed. A certain proportion of glycine can also be added.

Salts of O-acetylsalicylic acid with basic amino acids have been used for a long time in various indications, for instance in the abovementioned indications. The good solubility of these O-acetylsalicylates is an advantage here compared with O-acetylsalicylic acid, in particular in the case of parenteral administration. Moreover, in the case of relatively long oral administration good tolerability of the O-acetylsalicylates is to be emphasized.

A certain disadvantage of the O-acetylsalicylates until now was their inadequate stability. On the one hand, a restricted shelf life of the pharmaceutical preparations produced from these salts results from this. On the other hand, sterilization of the active compound, which may be necessary, cannot be carried out by means of heat sterilization because of the inadequate thermal stability of these salts, but must be carried out in other ways, for example by introduction of ethylene oxide gas.

The low stability of the O-acetylsalicylates is to be attributed to a back reaction of the product to O-acetylsalicylic acid and the corresponding amino acids known to the person skilled in the art. The amino acid then reacts with the O-acetylsalicylic acid with removal of the acetyl group (amidolysis) and release of salicylic acid. The presence of salicylic acid in pharmaceutical preparations, however, is undesirable and therefore to be restricted to a low, acceptable value. It is known that this degradation reaction is pH-dependent (F. Moll, Arch. Pharm. 318 (1985), 120–127). A lowering of the pH leads to an increased protonation of the amino acid released, so that this is not available or only available to a very restricted extent for the subsequent reaction with the O-acetylsalicylic acid. The amidolysis and thus the release of salicylic acid is thereby suppressed.

To increase the stability of pharmaceutical preparations which contain O-acetylsalicylates, the addition of "acidic" stabilizers such as calcium chloride has therefore been proposed in the past (cf. U.S. Pat. No. 4,265,888). The presence of Ca ions in the product, however, is not acceptable for the treatment of cardiovascular diseases.

It has likewise been postulated that the moisture content of the O-acetylsalicylate products has a considerable influence on their stability. Another way to increase the stability of the O-acetylsalicylates would therefore consist in the reduction of the residual moisture content by drying at a high temperature. Intensive drying at elevated temperature, however, because of the instability of the salts already mentioned above at the temperatures necessary therefor, leads to the desired goal only to a limited extent or not at all.

It was therefore the object of the present invention to make available compositions which comprise a salt of O-acetylsalicylic acid with a basic amino acid, and which have increased stability and therefore do not have the disadvantages of the O-acetylsalicylates known until now with respect to storage and/or sterilizability.

This object is achieved according to the present invention by a composition comprising a salt of O-acetylsalicylic acid with a basic amino acid, the salt having an average particle size above a particle size of 160 μm and a proportion of more than 60% of the particles having a particle size in a range from 100 to 200 μm in a particle size distribution measured using a Malvern 2600D apparatus under standard conditions.

According to the invention, compositions are preferred here in which the salt of O-acetylsalicylic acid with a basic amino acid contained therein has an average particle size above a particle size of 170 μm and a proportion of more than 70% of the particles having a particle size in a range from 100 to 200 μm in a particle size distribution measured using a Malvern 2600D apparatus under standard conditions.

The present invention is illustrated in greater detail by the accompanying figures, in which.

Figure 3:
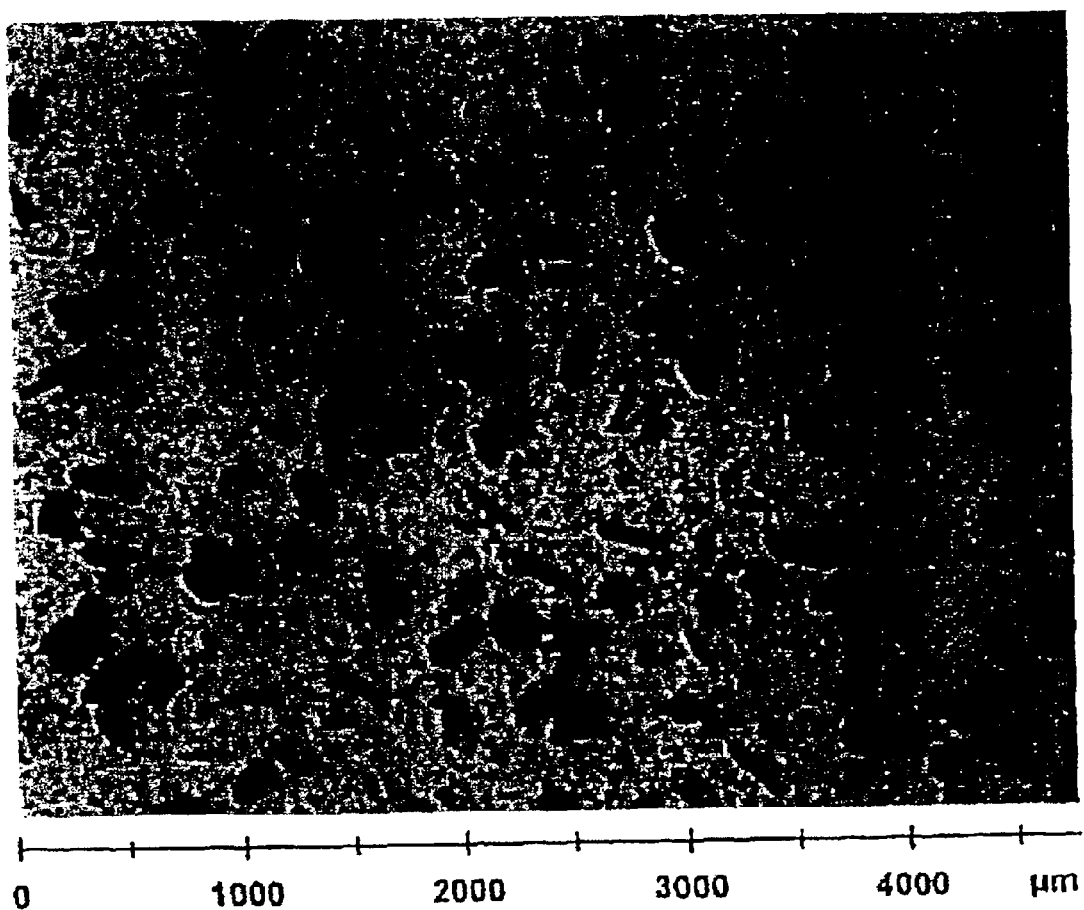
FIGS. 3 and 4 show illustrations of crystals of an O-acetylsalicylate according to Ex. 1 of the present invention.
Figure 4:
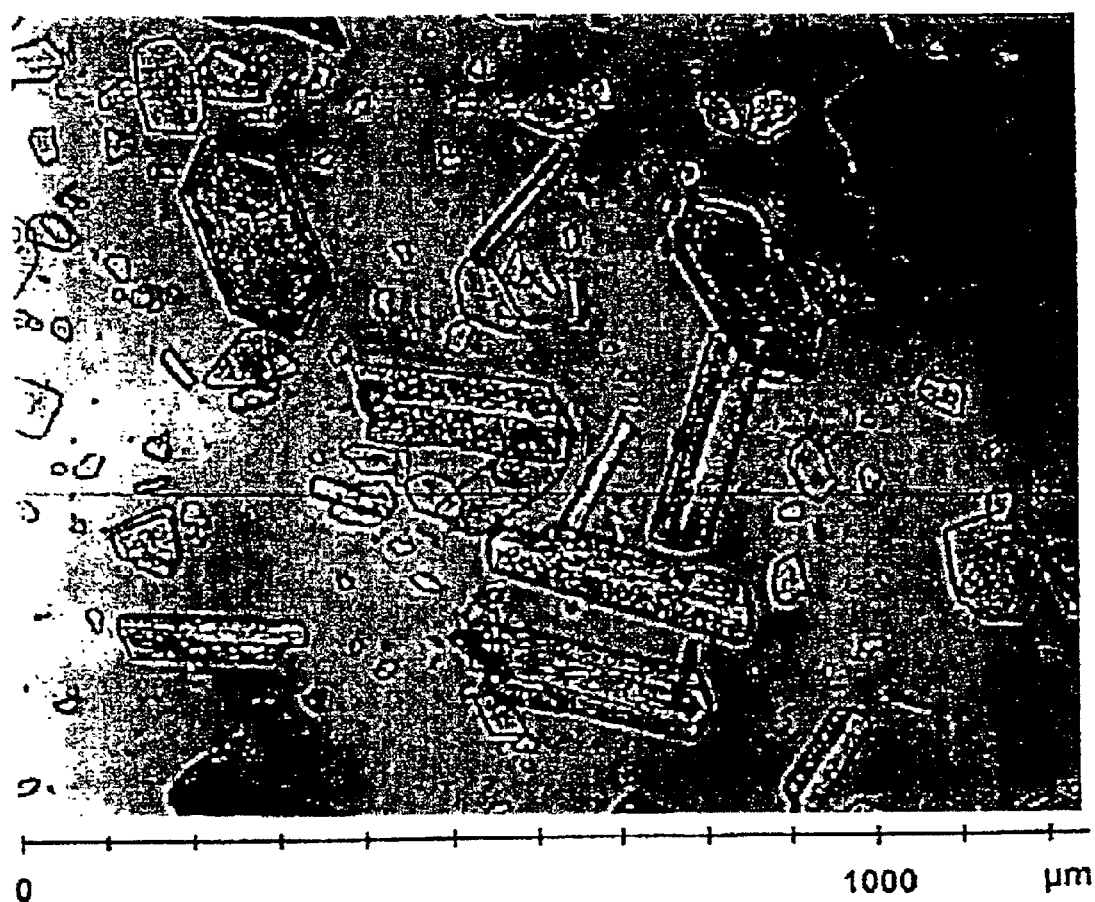
Figure 5:
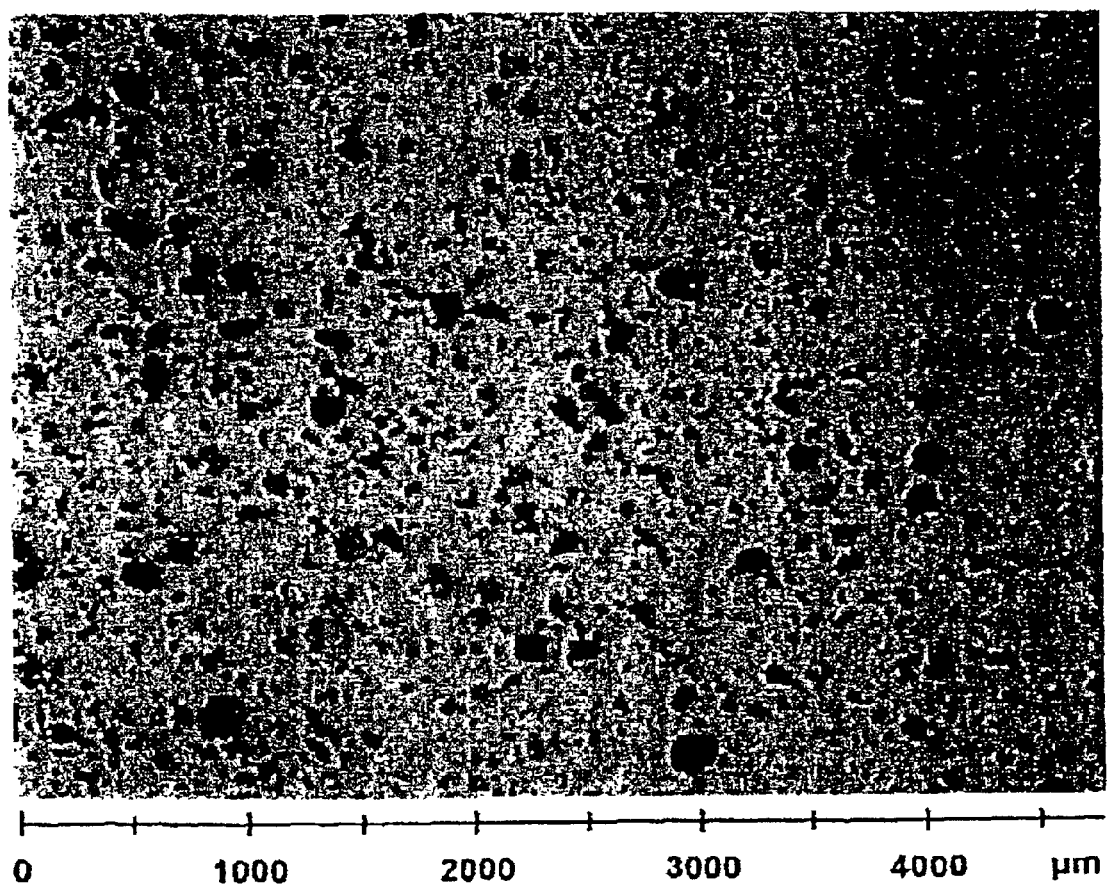
FIGS. 5 and 6 show illustrations of crystals of Aspisol®. The particle size analyses shown in FIGS. 1 and 2 were carried out using the same crystals.
Figure 6:
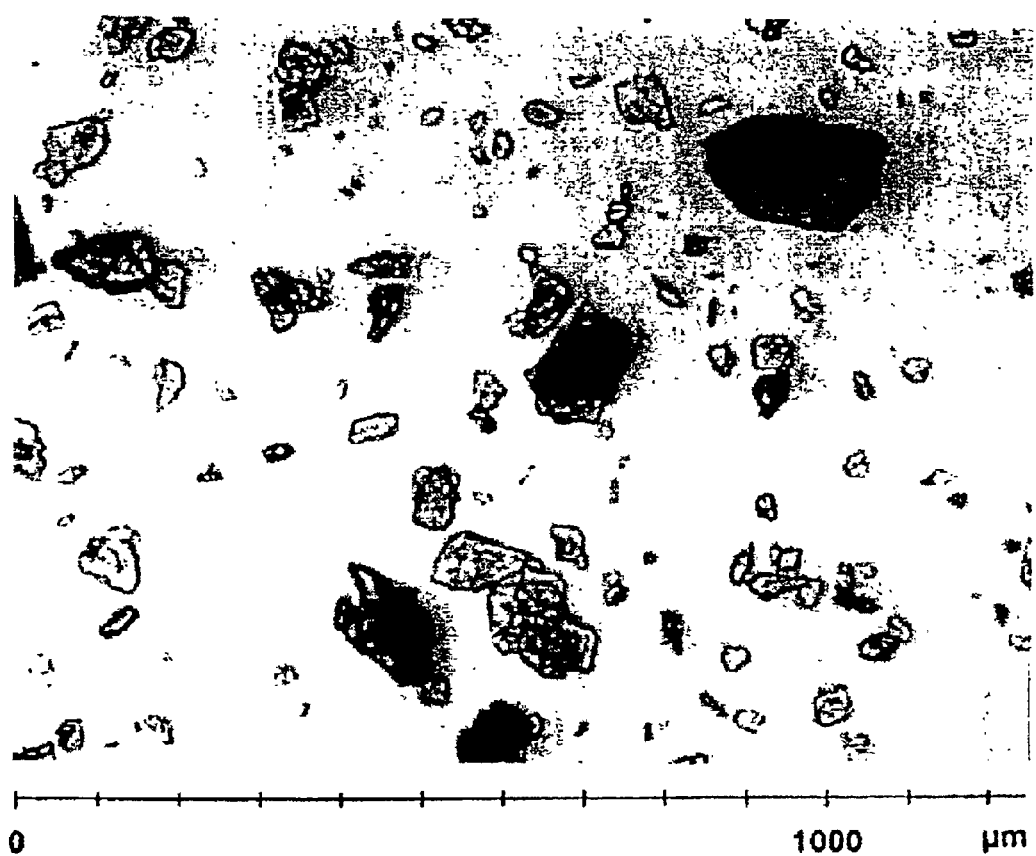

The O-acetylsalicylates according to the invention differ clearly and advantageously in their particle size analysis from the O-acetylsalicylates known until now. The distribution of the particle sizes in the case of the O-acetylsalicylates according to the invention is narrower and the average particle size is shifted to higher particle dimensions (cf. FIGS. 1 and 2). This means that the O-acetylsalicylates according to the invention consist of larger and more uniformly shaped (grown) crystals. In addition to a narrower particle size distribution and higher average particle size, the O-acetylsalicylates according to the invention additionally exhibit a highly pronounced crystal structure (cf. FIGS. 3 and 4). In comparison to this, the commercially obtainable O-acetylsalicylate Aspisol® has a clearly more poorly pronounced crystal structure (cf. FIGS. 5 and 6).

The advantageous properties of the O-acetylsalicylates described above surprisingly lead to the fact that the residual moisture content of the O-acetylsalicylates according to the invention can be kept extremely low and thus the back reaction of the O-acetylsalicylates to O-acetylsalicylic acid and the corresponding amino acid described above can be suppressed. This is all the more surprising, as O-acetylsalicylates per se are described as hygroscopic. The O-acetylsalicylates according to the invention, however, surprisingly have a reduced hygroscopicity. The O-acetylsalicylates according to the invention are clearly more stable at the same temperature than known acetylsalicylates having a higher residual moisture content.

The salts according to the invention have a residual moisture content of less than 0.4%, preferably of less than 0.3% and in particular of less than 0.15%, of water.

Figure 7:
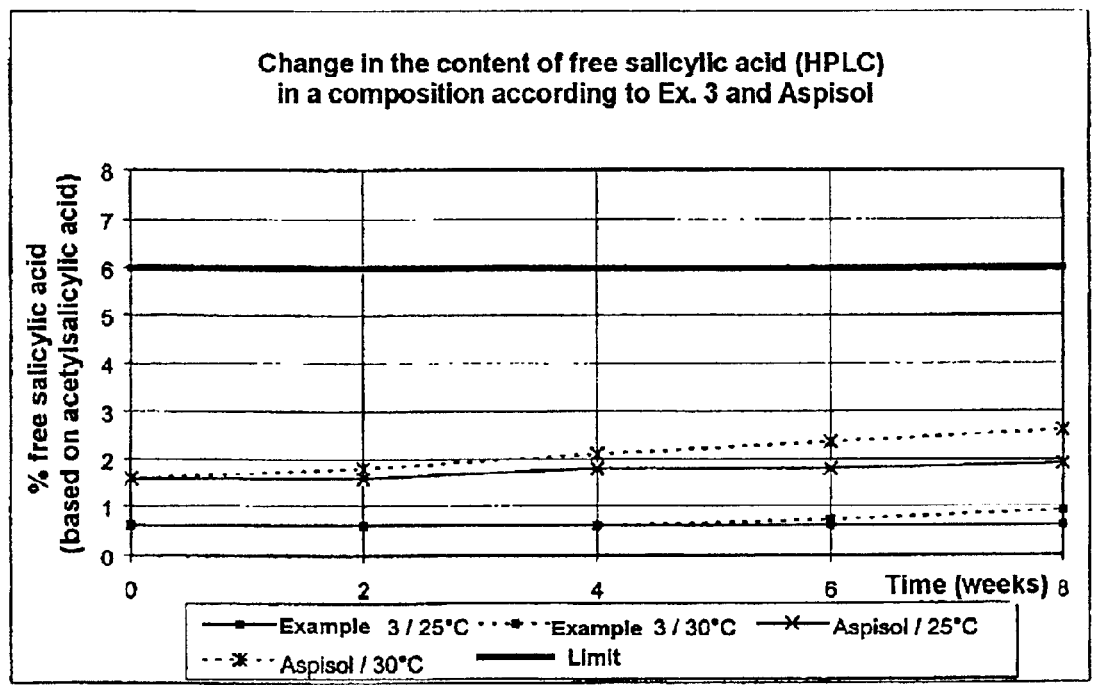
FIG. 7 shows a graphic representation of the stability at various temperatures. The change in the content of free salicylic acid (in %) in an O-acetylsalicylate according to Ex. 3 of the present invention and in Aspisol® is indicated.

As can be seen from FIG. 7, O-acetylsalicylates according to the invention which have a residual moisture content of less than 0.3% remain almost unchanged with respect to their proportion of free salicylic acid at a temperature of 25° C. over a period of 8 weeks, while O-acetylsalicylates having a residual moisture content of, for example, more than 0.4% undergo considerable degradation and an increase in the proportion of free salicylic acid. Thus the O-acetylsalicylates according to the invention prove to be stable over a long period at room temperature or with cooling.

The O-acetylsalicylates according to the invention can be prepared by the following process. All starting compounds are commercially obtainable. The amino acids which can be used according to the invention can occur in the L or in the D configuration or alternatively as a mixture of D and L forms. The term "amino acids" designates, according to the invention, in particular the α-amino acids occurring in nature, but moreover also includes their homologues, isomers and derivatives. Enantiomers can be mentioned as an example of isomers. Derivatives can be, for example, amino acids provided with protective groups. Typical examples of basic amino acids which may be mentioned are: lysine, arginine, ornithine, diaminobutyric acid.

According to the present invention, solutions of the reactants, i.e. of O-acetylsalicylic acid and the corresponding amino acid, are combined as rapidly as possible at a temperature below 30° C., preferably from 20 to 25° C., under normal pressure and blended to give a homogenous phase. Suitable solvents for the reactants are water or water-miscible organic solvents, for example alcohols such as methanol, ethanol or isopropanol, in particular ethanol, ethers such as tetrahydrofuran (THF) or ketones such as acetone.

The reactants are employed in amounts such that the basic amino acid is present in a slight excess. According to the invention, a ratio of O-acetylsalicylic acid to amino acid of 1:1.05 to 1:1.5 is preferred, a ratio of O-acetylsalicylic acid to amino acid of 1:1.05 to 1:1.2 being particularly preferred.

According to the present invention, the O-acetylsalicylic acid solution should contain from 1 to 10% by weight, preferably 5 to 10% by weight and particularly preferably from 6 to 8% by weight, of O-acetylsalicylic acid. The solution of the basic amino acid should contain from 10 to 40% by weight, preferably 15 to 35% by weight and particularly preferably from 20 to 30% by weight, of amino acid.

The crystallization of the composition according to the invention then takes place from the homogeneous mixture prepared in this way, if appropriate with addition of seed crystals, with addition of a clear excess of acetone in comparison with the reactants, for example of a 20 to 50% strength, preferably of a 30 to 40% strength, excess. It is very important according to the present invention that the temperature of the crystallization phase is kept within limits which are as narrow as possible. The temperature must not exceed 40° C. and should preferably be kept below 35° C. According to the invention, a temperature below 25° C., in particular of 0° C., is preferred. As seed crystals, crystals of the desired products, for example Aspisol® crystals, can be used. The crystallization is carried out under normal pressure.

Likewise important in the process according to the invention is the maintenance of a specific stirring energy during the crystallization. The homogeneous mixture of the starting products may only be stirred gently. The stirring energy to be applied should be not greater than 0.1 W per liter of reaction medium. According to the invention, an applied stirring energy of 0.04 to 0.06 W per liter of reaction medium is preferred. Possible stirrers are all conventional, accordingly controllable, stirrers such as a stirring unit container with baffles.

For crystallization, the solution should be kept under the conditions indicated above for not longer than 20 hours. According to the invention a crystallization time of less than 10 hours under the conditions indicated above is preferred, a time of 1 to 8 hours being particularly preferred.

If desired, the composition according to the invention can also contain glycine. The amount of glycine is freely selectable. According to the invention, a proportion of 5 to 30% by weight, particularly preferably of 5 to 15% by weight and especially preferably of 10% by weight, of glycine in the reaction solution is preferred.

According to the present invention, the glycine can be added to the reaction mixture of the reactants as a solution in water or a water-miscible organic solvent, it being possible to use the solvents described above as organic solvents. Glycine shows inert behaviour to these reactants. Under the conditions according to the invention mentioned above, processes of crystallization of the two solids (O-acetylsalicylate and glycine) from the homogeneous phase can thereby be carried out (cocrystallization).

According to the present invention, however, the glycine can also be added in the form of a suspension to an already crystallized suspension of the O-acetylsalicylate. The glycine suspension can be prepared in a conventional manner. According to the invention, the preparation of a glycine suspension from a solvent mixture of water and an alcohol such as ethanol is preferred.

The manner of the addition of the glycine has no influence on the properties of the composition according to the invention. It is to be noted that the addition of glycine to the compositions according to the invention is not necessary. In particular, the presence of glycine has no influence on the stability of the compositions according to the invention.

The crystallizate is then isolated in a conventional manner, for example by filtering or centrifuging. The solid is washed a number of times with organic solvents, alcohols according to the invention such as ethanol and/or ketones such as acetone or mixtures of alcohols or ketones, for example mixtures of ethanol and acetone, or the use of various solvents of this type being preferred.

The solid is then dried under reduced pressure. The temperature here should be kept below 50° C., preferably below 40° C. and particularly preferably below 35° C. A pressure of less than 50 mbar, preferably of less than 30 mbar, should be applied to the solid. The drying can be carried out under conventional conditions, for example in a drying apparatus.

The process according to the invention can also be completely carried out under sterile conditions. The differences from the above procedure necessary for this, for example with respect to sterilization of the starting compounds and the apparatus employed, are known to the person skilled in the art.

The compositions according to the invention can be employed as analgesics, antipyretics, antirheumatics, and also as non-steroidal anti-inflammatory agents, for example for the treatment of diseases of the rheumatic type, neuralgia, myalgia, and migraine. In particular, however, they can also be employed as platelet aggregation inhibitors in the prevention and therapy of cardiovascular and cerebrovascular diseases (e.g. in ischaemic heart diseases, stroke, stable and unstable angina pectoris, acute myocardial infarct, bypass operations, PTCA, stent implantation). Further application areas are stimulation of the immune system in HIV patients and tumour prophylaxis (e.g. carcinoma of the colon, oesophagus or lung), slowing of the cognitive deterioration in dementia syndrome (e.g. Alzheimer's disease), inhibition of gallstone formation and the treatment of diabetic diseases.

The present invention also includes pharmaceutical preparations which, in addition to non-toxic, inert pharmaceutically suitable vehicles, contain the compositions according to the invention, and processes for the production of these preparations.

The compositions according to the invention can optionally also be present in microencapsulated form in one or more of the vehicles indicated above.

The compositions according to the invention should be present in the abovementioned pharmaceutical preparations in a concentration of approximately 0.1 to 99.5, preferably of approximately 0.5 to 95, % by weight of the total mixture.

In a special embodiment of the invention, the abovementioned pharmaceutical preparations can also contain effective quantities of one or more further pharmaceutical active compounds apart from the compositions according to the invention as, in particular, one or more ADP receptor antagonists (as, for example, ticlopidine and clopidogrel), GPIIb/IIIa receptor antagonists (as, for example, abciximab, eptifabitide, tirofiban, orofiban, xemilofiban and sibrafiban), phosphodiesterase inhibitors (as, for example, dipyridamole), thrombin receptor antagonists (as, for example, hirudin, hirulog and argatroban), factor Xa inhibitors (as, for example, antistatin, DX-9065 and pentasaccharides), HMG-CoA receptor antagonists (as, for example, simvastatin and cerivastatin) and/or calcium antagonists (as, for example, nifedipine).

In general, it has proved advantageous both in human and in veterinary medicine to administer the active compound(s) according to the invention in total amounts of approximately 0.5 to approximately 500, preferably 5 to 100, mg/kg of body weight every 24 hours, if appropriate in the form of several individual doses, to achieve the desired results. An individual dose contains the active compound(s) according to the invention preferably in amounts from approximately 1 to approximately 80, in particular 3 to 30, mg/kg of body weight.

The active compound can act systemically and/or locally. For this purpose, it can be administered in a suitable manner, e.g. orally or parenterally. For these application routes the active compound can be administered in suitable administration forms.

For oral administration, known administration forms releasing the active compound rapidly and/or in modified form are suitable, such as tablets (uncoated and coated tablets, e.g. enteric coatings, FDT (fast-dissolve tablets), effervescent tablets, chewable tablets), capsules, coated tablets, granules, pellets, powders, emulsions, suspensions and solutions.

Parenteral administration can be carried out with circumvention of an absorption step (intravenous, intraarterial, intracardiac, intraspinal or intralumbar) or with insertion of an absorption (intramuscular, subcutaneous, intracutaneous or intraperitoneal). For parenteral administration, suitable administration forms are, inter alia, injection and infusion preparations in the form of solutions, suspensions, emulsions, lyophilizates and sterile powders.

Topical application in the form of suppositories or of transdermal systems (e.g. patches, ETS systems) and also in creams, ointments, gels, sprays or dissolved in organic or inorganic solvents are further administration possibilities.

The active compounds can be converted into the administration forms mentioned in a known manner. This is carried out using inert non-toxic, pharmaceutically suitable excipients. These include, inter alia, vehicles (e.g. microcrystalline cellulose), solvents (e.g. liquid polyethylene glycols), emulsifiers (e.g. sodium dodecylsulphate), dispersants (e.g. polyvinylpyrrolidone), synthetic and natural biopolymers (e.g. albumin), stabilizers (e.g. antioxidants such as ascorbic acid), colourants (e.g. inorganic pigments such as iron oxides) or taste and/or odour corrigents.

EXAMPLES

The present invention is presented in greater detail below with the aid of nonrestrictive preferred examples. If not stated otherwise, all quantitative data relate to percentages by weight.

Example 1

Lysine Acetylsalicylate

A pyrogen-free solution of 9.9 kg of O-acetylsalicylic acid in 120 kg of ethanol is added through a sterile filter to a sterile and pyrogen-free stirring unit container with baffles. A sterile-filtered pyrogen-free solution of 9.0 kg of lysine hydrate in 26.5 kg of pyrogen-free water is added within a short time at 20 to 25° C. and the solutions are mixed such that a temperature of 30° C. is not exceeded. 50 g of seed crystals are added and the already crystallizing mixture is mixed with 120 kg of sterile-filtered acetone with cooling to 0° C. The mixture is allowed to crystallize for 1 to 8 hours with gentle stirring at 0° C. The crystallizate is isolated under aseptic conditions on a filter or a centrifuge. The moist product is washed a number of times with ethanol in a separating apparatus. The moist product is transferred to a dryer under aseptic conditions and dried therein at a pressure of less than 30 mbar at a temperature of not more than 40° C.

89 to 94% of the desired product was obtained, which had a residual moisture content of 0.10 to 0.15%.

Example 2

D,L-Lysine Acetylsalicylate with 10% of Glycine

A pyrogen-free solution of 9.9 kg of O-acetylsalicylic acid in 145 kg of ethanol is added through a sterile filter to a sterile and pyrogen-free stirring unit container with baffles. A sterile-filtered pyrogen-free solution of 9.0 kg of D,L-lysine hydrate and 2.4 kg of glycine in 35 kg of pyrogen-free water is added within a short time at 20 to 25° C. and the solutions are mixed such that a temperature of 30° C. is not exceeded. 50 g of seed crystals are added and the already crystallizing mixture is mixed with 120 kg of sterile-filtered acetone with cooling to 0° C. The mixture is allowed to crystallize for 1 to 8 hours with gentle stirring at 0° C. The crystallizate is isolated under aseptic conditions on a filter or a centrifuge. The moist product is washed successively with ethanol and acetone in a separating apparatus. The moist product is transferred to a dryer under aseptic conditions and dried therein at a pressure of less than 30 mbar at a temperature of not more than 40° C.

90 to 95% of the desired product was obtained, which had a residual moisture content of 0.10 to 0.15%.

Example 3

D,L-Lysine Acetylsalicylate with 10% of Glycine

A pyrogen-free solution of 9.9 kg of O-acetylsalicylic acid in 120 kg of ethanol is added through a sterile filter to a sterile and pyrogen-free stirring unit container with baffles. A sterile-filtered pyrogen-free solution of 9.0 kg of lysine hydrate in 26.5 kg of pyrogen-free water is added within a short time at 20 to 25° C. and the solutions are mixed such that a temperature of 30° C. is not exceeded. 50 g of seed crystals are added and the already crystallizing mixture is mixed with 120 kg of sterile-filtered acetone with cooling to 0° C. The mixture is allowed to crystallize for 1 to 8 hours with gentle stirring at 0° C. An aseptic suspension of 2.1 kg of glycine in 8 kg of pyrogen-free water and 25 kg of ethanol is prepared in a separate sterile and pyrogen-free stirring unit container. This is added to the salicylate suspension. The crystal mixture is isolated under aseptic conditions on a filter or a centrifuge. The moist product is washed a number of times with ethanol in a separating apparatus. The moist product is transferred to a dryer under aseptic conditions and dried therein at a pressure of less than 30 mbar at a temperature of not more than 40° C.

89 to 94% of the desired product was obtained, which had a residual moisture content of 0.10 to 0.15%.

Determination of the Particle Size Distribution

The compositions according to the invention and commercially available Aspisol® (marketed by Bayer AG) were investigated in a Malvern 2600 D measuring apparatus from Malvern under the following standard conditions.

The Malvern 2600 measuring apparatus consists of an He/Ne laser, a measuring cuvette having a thermostatted reservoir system, Fourier lenses and multielement detector. The measured light intensities are converted into a particle size distribution. The alignment of laser and lens is adjusted manually before each measurement and the measuring apparatus is checked by means of a blank measurement. The blank pulses must not exceed a highest value of 20 per detector element.

The sample to be investigated is shaken by hand for about 15 s; a sample is then taken with a spatula. The amount of sample depends on the permissible obscuration area (0.1-0.3) of the measuring apparatus. The sample taken is gently predispersed in a beaker (by stirring with a glass rod) using a customary dispersing agent such as Baysilon M10® (Bayer AG) and then filled into the reservoir of the measuring apparatus, which is likewise filled with the dispersant. The beaker is rinsed out completely with the dispersant in order to guarantee representative sampling.

The measurement is carried out using a set focal length of 300 mm, thermostatting at 20° C. and a permissible obscuration area of 0.1–0.3.

The product is measured after ultrasonication times of 0, 15 and 60 seconds. For this, the ultrasonic finger is situated in the reservoir of the product circulation. The suspension is pumped through the measuring cuvette in a closed circulation. The signals recorded by the detector are analysed and converted into the particle size distribution.

Figure 1:
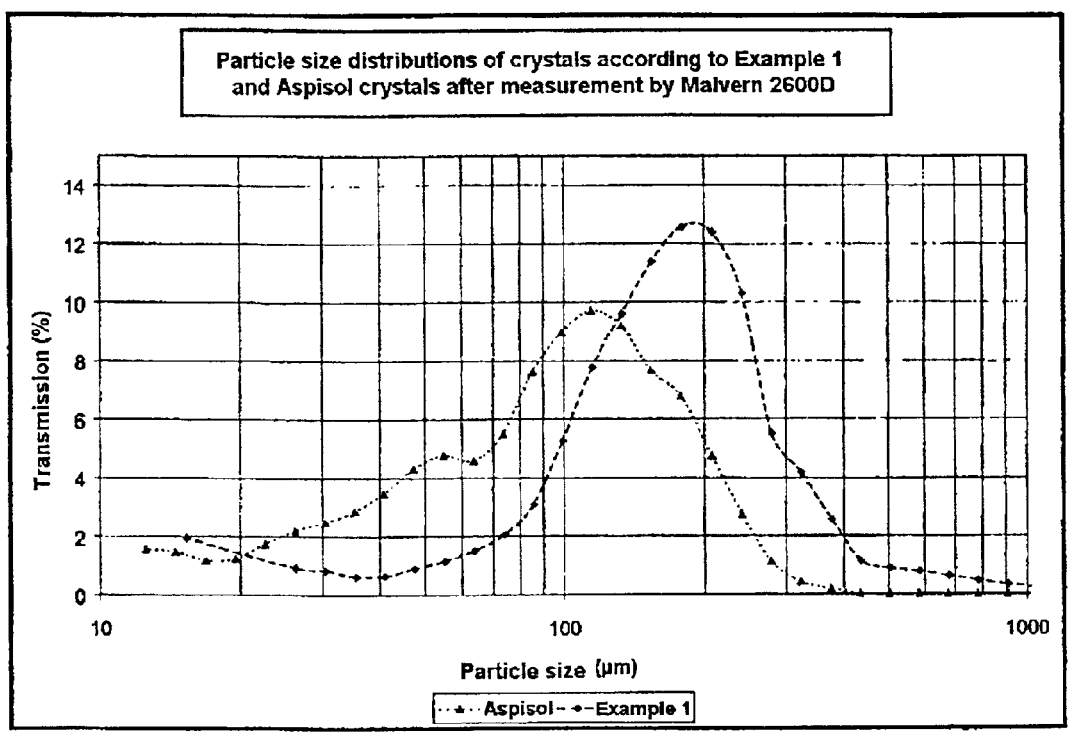
FIG. 1 shows a graphic representation of the particle size distribution of the O-acetylsalicylate prepared according to Ex. 1 in comparison with the particle size distribution of a commercially available O-acetylsalicylate (Aspisol®)
Figure 2:
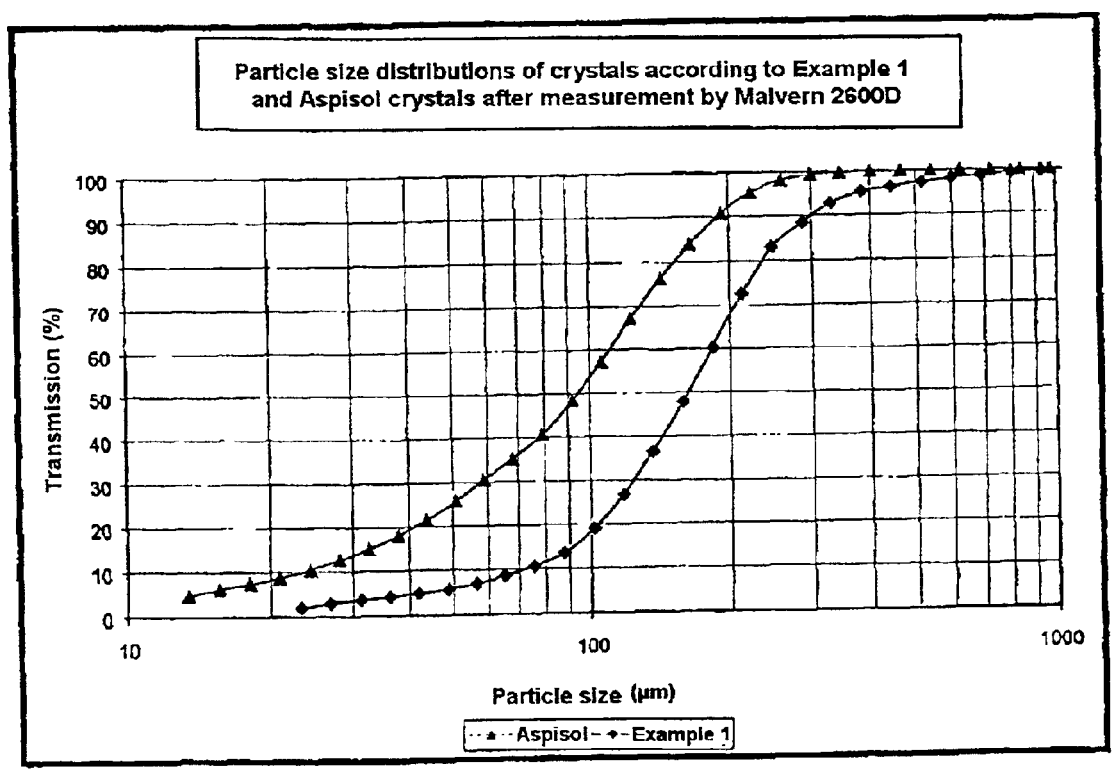
FIG. 2 shows the integrals of the curves of the particle size distributions shown in FIG. 1 for Ex. 1 according to the invention and Aspisol®

The results thus obtained are shown in FIGS. 1 and 2.

What is claimed is:

1. A composition of matter comprising salt crystals formed by combining o-acetylsalicylic acid with a basic amino acid, wherein said salt crystals have an average particle size above about 160 $\mu$m, wherein more than about 60% of the crystals in said composition have a particle size from about 100 $\mu$m, to about 200 $\mu$m, wherein said particle size is measured by laser diffraction.

2. The composition of claim 1, wherein said salt crystals have an average particle size above about 170 $\mu$m and wherein more than about 70% of said crystals in said composition have a particle size from about 100 $\mu$m to about 200 $\mu$m.

3. The composition of claim 1, wherein said basic amino acid is selected from the group consisting of lysine, arginine, histidine, ornithine and diaminobutyric acid.

4. The composition of claim 3, wherein said basic amino acid is lysine.

5. The composition of claim 1, further comprising from about 5% to about 15% by weight of glycine.

6. The composition of claim 5, wherein said composition comprises about 10% by weight of glycine.

7. A process for the making a particulate salt composition comprising the steps of:
    (a) Rapidly combining a first solution of o-acetylsalicylic acid and a slight excess of a second solution of a basic amino acid in water or a water-miscible organic solvent at a temperature below about 30° C. under normal pressure, to form a first mix;
    (b) Adding acetone to said first mix at a temperature below about 40° C. at normal pressure to form a second mix;
    (c) Stirring said second mix for not longer than 20 hours at a stirring energy of not more than 0.1 W per liter of reaction medium, to form a first precipitate and a first solute;
    (d) Isolating said first precipitate from said first solute;
    (e) Washing said first precipitate;
    (f) Drying said first precipitate at a temperature below about 50° C. and at a pressure below about 50 mbar, and
    (g) Sizing said first precipitate to form salt crystals having an average particle size above about 160 $\mu$m, wherein more than about 60% of the salt crystals in said composition have a particle size from about 100 $\mu$m to about 200 $\mu$m, wherein said particle size is measured by laser diffraction.

8. The process of claim 7, wherein the step of rapidly combining said first solution and said second solution is carried out at a temperature from about 20° C. to about 25° C. and at atmospheric pressure.

9. The process of claim 7, wherein the molar ratio of o-acetylsalicylic acid to amino acid is from about 1:1.05 to about 1:1.2.

10. The process of claim 7, wherein said second mix is added in a molar excess of from about 30% to about 40% with respect to said first mix.

11. The process of claim 10, wherein the temperature of said first mix and said second mix is maintained at about 0° C.

12. The process of claim 10, wherein said step of stirring is carried out for a time from about one to about eight hours.

13. The process of claim 7, wherein said step of stirring is carried out at a stirring energy from about 0.04 to 0.06 W per liter of reaction medium.

14. The process of claim 7, wherein said step of drying is carried out at a temperature below about 35° C.

15. The process of claim 7, wherein said step of drying is carried out at a pressure of less than about 30 mbar.

16. The process of claim 7, further comprising the step of adding about 10% by weight of glycine to said first mix or said second mix.

17. The process of claim 16, wherein said glycine is added at 10% by weight.

18. The process of claim 7, further comprising the step of adding seed crystals to said second mix at a temperature below 40° C. at normal pressure.

19. The process of claim 7, wherein said process is carried out under sterile conditions.

20. A medicament comprising the composition of claim 1.

21. The medicament of claim 20, further comprising at least one additional pharmaceutical active ingredient selected from the group consisting of ADP receptor antagonists, GPIIb/IIIa receptor antagonists, phosphodiesterase inhibitors, thrombin receptor antagonists, factor Xa inhibitors, HMG-CoA receptor antagonists and calcium antagonists.

* * * * *